(12) United States Patent
Barreiro et al.

(10) Patent No.: US 11,013,614 B2
(45) Date of Patent: *May 25, 2021

(54) EXPANDABLE INTERBODY FUSION DEVICE

(71) Applicant: SPINE WAVE, INC., Shelton, CT (US)

(72) Inventors: Peter Barreiro, West Haven, CT (US); Dennis Ty, Carlsbad, CA (US); Michael E. Landry, Austin, TX (US)

(73) Assignee: SPINE WAVE, INC., Shelton, CT (US)

( * ) Notice: Subject to any disclaimer, the term of this patent is extended or adjusted under 35 U.S.C. 154(b) by 104 days.

This patent is subject to a terminal disclaimer.

(21) Appl. No.: 16/407,316

(22) Filed: May 9, 2019

(65) Prior Publication Data

US 2019/0262141 A1 Aug. 29, 2019

Related U.S. Application Data

(63) Continuation of application No. 15/989,719, filed on May 25, 2018, now Pat. No. 10,292,835, which is a
(Continued)

(51) Int. Cl.
| | |
|---|---|
| *A61F 2/44* | (2006.01) |
| *A61F 2/46* | (2006.01) |
| *A61F 2/30* | (2006.01) |

(52) U.S. Cl.
CPC .......... *A61F 2/447* (2013.01); *A61F 2/30771* (2013.01); *A61F 2/442* (2013.01);
(Continued)

(58) Field of Classification Search
CPC .... A61F 2/46; A61F 2/44; A61F 2/442; A61F 2/447; A61F 2/30; A61F 2/30771
See application file for complete search history.

(56) References Cited

U.S. PATENT DOCUMENTS

| | | |
|---|---|---|
| 3,486,505 A | 12/1969 | Morrison |
| 4,524,766 A | 6/1985 | Petersen |
(Continued)

FOREIGN PATENT DOCUMENTS

| | | |
|---|---|---|
| EP | 0621020 | 10/1994 |
| FR | 2639823 | 6/1990 |
(Continued)

OTHER PUBLICATIONS

Medtronic Sofamor Danek, "VERTE-STACK™ PEEk Stackable Corpectomy Device, Surgical Technique" (date unknown), (8 pp.).
(Continued)

*Primary Examiner* — Christopher J Beccia
(74) *Attorney, Agent, or Firm* — Hoffmann & Baron, LLP

(57) ABSTRACT

An expandable interbody fusion device includes superior and inferior endplates that are configured to receive a sequentially inserted stack of interlocking expansion members or wafers. The like-configured wafers include features on their top and bottom surfaces that interlock the wafers in multiple degrees of freedom so that the wafer stack is not disrupted when the fusion device is fully expanded. One of the interlocking features includes a plurality of prongs projecting from an upper surface of the wafers and into a recess defined in the lower surface of an adjacent previously inserted like-configured wafer. The prongs and recesses are configured to prevent retrograde movement of each new wafer in a direction opposite the direction of insertion. Other interlocking features prevent movement in the direction of insertion, transverse to the insertion direction and vertically within the stack.

16 Claims, 10 Drawing Sheets

Related U.S. Application Data continuation of application No. 15/468,362, filed on Mar. 24, 2017, now Pat. No. 9,980,827, which is a continuation of application No. 15/193,726, filed on Jun. 27, 2016, now Pat. No. 9,610,175, which is a continuation of application No. 14/810,706, filed on Jul. 28, 2015, now Pat. No. 9,381,094, which is a continuation of application No. 14/547,249, filed on Nov. 19, 2014, now Pat. No. 9,095,447, which is a continuation of application No. 14/072,161, filed on Nov. 5, 2013, now Pat. No. 8,900,313, which is a continuation of application No. 13/736,514, filed on Jan. 8, 2013, now Pat. No. 8,574,299, which is a continuation of application No. 13/166,375, filed on Jun. 22, 2011, now Pat. No. 8,349,014, which is a continuation of application No. 11/756,050, filed on May 31, 2007, now Pat. No. 7,667,867.

(52) U.S. Cl.
CPC .......... *A61F 2/4455* (2013.01); *A61F 2/4611* (2013.01); *A61F 2/4637* (2013.01); *A61F 2/30965* (2013.01); *A61F 2/4425* (2013.01); *A61F 2002/305* (2013.01); *A61F 2002/3055* (2013.01); *A61F 2002/30403* (2013.01); *A61F 2002/30428* (2013.01); *A61F 2002/30522* (2013.01); *A61F 2002/30574* (2013.01); *A61F 2002/30579* (2013.01); *A61F 2002/30599* (2013.01); *A61F 2002/30604* (2013.01); *A61F 2002/30904* (2013.01); *A61F 2220/0025* (2013.01); *A61F 2250/0063* (2013.01)

(56) References Cited

U.S. PATENT DOCUMENTS

| | | | |
|---|---|---|---|
| 4,683,476 A | 7/1987 | Ferrari et al. | |
| 4,736,738 A | 4/1988 | Lipovsek et al. | |
| 4,755,797 A | 7/1988 | Kanaya | |
| 4,863,476 A | 9/1989 | Shepperd | |
| 4,888,024 A | 12/1989 | Powlan | |
| 5,059,193 A | 10/1991 | Kuslich | |
| 5,192,326 A | 3/1993 | Bao et al. | |
| 5,192,327 A | 3/1993 | Brantigan | |
| 5,197,971 A | 3/1993 | Bonutti | |
| 5,298,254 A | 3/1994 | Prewett et al. | |
| 5,431,658 A | 7/1995 | Moskovich | |
| 5,439,684 A | 8/1995 | Prewett et al. | |
| 5,505,732 A | 4/1996 | Michelson | |
| 5,514,180 A | 5/1996 | Heggeness et al. | |
| 5,522,899 A | 6/1996 | Michelson | |
| 5,554,191 A | 9/1996 | Lahille et al. | |
| 5,571,109 A | 11/1996 | Bertagnoli | |
| 5,591,235 A | 1/1997 | Kuslich | |
| 5,620,458 A | 4/1997 | Green et al. | |
| 5,645,599 A | 7/1997 | Samani | |
| 5,653,763 A | 8/1997 | Errico et al. | |
| 5,658,335 A | 8/1997 | Allen | |
| 5,702,454 A | 12/1997 | Baumgartner | |
| 5,755,797 A | 5/1998 | Baumgartner | |
| 5,756,127 A | 5/1998 | Grisoni et al. | |
| 5,836,948 A | 11/1998 | Zucherman et al. | |
| 5,860,977 A | 1/1999 | Zucherman et al. | |
| 5,865,848 A | 2/1999 | Baker | |
| 5,891,147 A | 4/1999 | Moskovitz et al. | |
| 5,904,719 A | 5/1999 | Errico et al. | |
| 5,951,553 A | 9/1999 | Betz et al. | |
| 5,980,522 A | 11/1999 | Koros et al. | |
| 6,033,411 A | 3/2000 | Preissman | |
| 6,045,579 A | 4/2000 | Hochschuler et al. | |
| 6,066,154 A | 5/2000 | Reiley et al. | |
| 6,074,390 A | 6/2000 | Zucherman et al. | |
| 6,102,950 A | 8/2000 | Vaccaro | |
| 6,110,179 A | 8/2000 | Flivik et al. | |
| 6,110,210 A | 8/2000 | Norton et al. | |
| 6,159,211 A | 12/2000 | Boriani et al. | |
| 6,159,244 A | 12/2000 | Suddaby | |
| 6,176,882 B1 | 1/2001 | Biedermann et al. | |
| 6,190,414 B1 | 2/2001 | Young et al. | |
| 6,193,757 B1 | 2/2001 | Foley et al. | |
| 6,200,347 B1 | 3/2001 | Anderson et al. | |
| 6,241,771 B1 | 6/2001 | Gresser et al. | |
| 6,273,916 B1 | 8/2001 | Murphy | |
| 6,279,916 B1 | 8/2001 | Stecher | |
| 6,287,308 B1 | 9/2001 | Betz et al. | |
| 6,287,309 B1 | 9/2001 | Baccelli et al. | |
| 6,387,130 B1 | 5/2002 | Stone et al. | |
| 6,395,034 B1 | 5/2002 | Suddaby | |
| 6,402,750 B1 | 6/2002 | Atkinson et al. | |
| 6,419,705 B1 | 7/2002 | Erickson | |
| 6,432,107 B1 | 8/2002 | Ferree | |
| 6,436,142 B1 | 8/2002 | Paes et al. | |
| 6,447,544 B1 | 9/2002 | Michelson | |
| 6,478,800 B1 | 11/2002 | Fraser et al. | |
| 6,488,710 B2 | 12/2002 | Besselink | |
| 6,500,205 B1 | 12/2002 | Michelson | |
| 6,562,074 B2 | 5/2003 | Gerbec et al. | |
| 6,572,653 B1 | 6/2003 | Simonson | |
| 6,595,998 B2 | 7/2003 | Johnson et al. | |
| 6,620,196 B1 | 9/2003 | Trieu | |
| 6,648,917 B2 | 11/2003 | Gerbec et al. | |
| 6,656,178 B1 | 12/2003 | Veldhuizen et al. | |
| 6,726,691 B2 | 4/2004 | Osorio et al. | |
| 6,740,093 B2 | 5/2004 | Hochschuler et al. | |
| 6,837,904 B2 | 1/2005 | Ralph et al. | |
| 6,852,095 B1 | 2/2005 | Ray | |
| 6,852,126 B2 | 2/2005 | Ahlgren | |
| 6,852,129 B2 | 2/2005 | Gerbec et al. | |
| 6,863,673 B2 | 3/2005 | Gerbec et al. | |
| 6,997,929 B2 | 2/2006 | Manzi et al. | |
| 7,118,580 B1 | 10/2006 | Beyersdorff et al. | |
| 7,153,325 B2 | 12/2006 | Kim et al. | |
| 7,311,713 B2 | 12/2007 | Johnson et al. | |
| 7,591,852 B2 | 9/2009 | Prosser | |
| 7,682,397 B2 | 3/2010 | Berry et al. | |
| 7,771,473 B2 | 8/2010 | Thramann | |
| 7,780,707 B2 | 8/2010 | Johnson et al. | |
| 8,715,351 B1 | 5/2014 | Pinto | |
| 8,900,312 B2 | 12/2014 | McLean et al. | |
| 9,980,827 B2 * | 5/2018 | Barreiro ............... A61F 2/4637 |
| 2002/0026195 A1 | 2/2002 | Layne et al. | |
| 2002/0107574 A1 | 8/2002 | Boehm, Jr. et al. | |
| 2002/0128716 A1 | 9/2002 | Cohen et al. | |
| 2002/0147497 A1 | 10/2002 | Belef et al. | |
| 2002/0177897 A1 | 11/2002 | Michelson | |
| 2002/0183761 A1 | 12/2002 | Johnson et al. | |
| 2003/0065396 A1 | 4/2003 | Michelson | |
| 2003/0130739 A1 | 7/2003 | Gerbec et al. | |
| 2003/0171812 A1 | 9/2003 | Grunberg et al. | |
| 2004/0019354 A1 | 1/2004 | Johnson et al. | |
| 2004/0064144 A1 | 4/2004 | Johnson et al. | |
| 2004/0087947 A1 | 5/2004 | Lim et al. | |
| 2004/0153065 A1 | 8/2004 | Lim | |
| 2004/0220580 A1 | 11/2004 | Johnson et al. | |
| 2005/0027364 A1 | 2/2005 | Kim et al. | |
| 2005/0038512 A1 | 2/2005 | Michelson | |
| 2005/0060034 A1 | 3/2005 | Berry et al. | |
| 2005/0107878 A1 | 5/2005 | Conchy | |
| 2005/0125062 A1 | 6/2005 | Biedermann et al. | |
| 2005/0149194 A1 | 7/2005 | Ahlgren | |
| 2005/0228500 A1 | 10/2005 | Kim et al. | |
| 2006/0058807 A1 | 3/2006 | Landry et al. | |
| 2006/0058880 A1 | 3/2006 | Wysocki et al. | |
| 2006/0122701 A1 | 6/2006 | Kiester | |
| 2006/0129244 A1 | 6/2006 | Ensign | |
| 2008/0300598 A1 | 12/2008 | Barreiro et al. | |
| 2010/0179656 A1 | 7/2010 | Theofilos | |

FOREIGN PATENT DOCUMENTS

| | | |
|---|---|---|
| FR | 2719763 | 11/1995 |
| WO | 9902214 | 1/1999 |

(56) References Cited

FOREIGN PATENT DOCUMENTS

OTHER PUBLICATIONS

Signus Medical, "Tetris", Sep. 2003, (1 p.).
Blackstone Medical, Inc., "CONSTRUX™ PEEK VBR System", 2005, (1 p.).
Globus Medical, "SUSTAIN™ R Small" (date unknown), (6 p.).
Baddeley, S., et al; "The Use of Methylmethacrylate in the Treatment of Giant Tumors of the Proximal Tibia", Aust. N.Z. J. Surg., vol. 49, No. 1, Feb. 1979, (3 pp.).
Campanacci, M., et al.; "The Treatment of Tibial Plateau Fractures", Chi. Org. Mov. 72(3), Dec. 1975, Italian text (pp. 234-256) English translation.
Kyphon Surgical Technique Manual, 1999 (pp. 5, 6, 9, 16-19).
Kyphon Vertebral Treatment Notebook, "Treatment for vertebral body compression fractures and back pain", date unknown, (9 pp).
Kyphon web page, www.kyphon.com, Mar. 13, 2001, (1 p.).
AOM Techniques Manual, "Controlled Delivery for Osteoplasty—A Vertebroplasty Application", date unknown, (11 pp.).
PCT Search Report for corresponding PCT Application No. PCT/US2008/064534.
http://www.thefreedictionary.com/constrict, definition of "Constrict", accessed Jan. 11, 2018.
www.thefreedictionary.com/elongate, definition of "Elongate", accessed Jan. 11, 2018.

\* cited by examiner

EXPANDABLE INTERBODY FUSION DEVICE

CROSS-REFERENCES TO RELATED APPLICATIONS

This application is a continuation of U.S. application Ser. No. 15/989,719, filed May 25, 2018, now U.S. Pat. No. 10,292,835, which is a continuation of U.S. application Ser. No. 15/468,362, filed Mar. 24, 2017, now U.S. Pat. No. 9,980,827, which is a continuation of U.S. application Ser. No. 15/193,726, filed Jun. 27, 2016, now U.S. Pat. No. 9,610,175, which is a continuation of U.S. application Ser. No. 14/810,706, filed Jul. 28, 2015, now U.S. Pat. No. 9,381,094, which is a continuation of U.S. application Ser. No. 14/547,249, filed Nov. 19, 2014, now U.S. Pat. No. 9,095,447, which is a continuation of U.S. application Ser. No. 14/072,161, filed Nov. 5, 2013, now U.S. Pat. No. 8,900,313, which is a continuation of U.S. application Ser. No. 13/736,514, filed Jan. 8, 2013, now U.S. Pat. No. 8,574,299, which is a continuation of U.S. application Ser. No. 13/166,375, filed Jun. 22, 2011, now U.S. Pat. No. 8,349,014, which is a continuation of U.S. application Ser. No. 11/756,050, filed May 31, 2007, now U.S. Pat. No. 7,967,867, the entire contents of which are incorporated by reference herein.

BACKGROUND OF THE INVENTION

The present invention relates to devices and methods for distraction and stabilization of tissue surfaces, and most particularly for stabilization of the intervertebral disc space in interbody fusion applications.

The number of spinal surgeries to correct the causes of low back pain has steadily increased over the last several years. Most often, low back pain originates from damage or defects in the spinal disc between adjacent vertebrae. The disc can be herniated or can be suffering from a variety of degenerative conditions, so that in either case the anatomical function of the spinal disc is disrupted. The most prevalent surgical treatment for these types of conditions has been to fuse the two vertebrae surrounding the affected disc. In most cases, the entire disc will be removed, except for the annulus, by way of a discectomy procedure. Since the damaged disc material has been removed, something must be positioned within the intra-discal space, otherwise the space may collapse resulting in damage to the nerves extending along the spinal column.

In order to prevent this disc space collapse, the intra-discal space has been filled with bone or a bone substitute in order to fuse the two adjacent vertebrae together. In early techniques, bone material was simply disposed between the adjacent vertebrae, typically at the posterior aspect of the vertebrae, and the spinal column was stabilized by way of a plate or a rod spanning the affected vertebrae. With this technique, once fusion has occurred the hardware used to maintain the stability of the segment became superfluous. Moreover, the surgical procedures necessary to implant a rod or plate to stabilize the level during fusion were frequently lengthy and involved.

It was therefore determined that a more optimum solution to the stabilization of an excised disc space is to fuse the vertebrae between their respective end plates, most optimally without the need for anterior or posterior plating. There have been an extensive number of attempts to develop an acceptable intra-discal implant that could be used to replace a damaged disc and yet maintain the stability of the disc interspace between the adjacent vertebrae, at least until complete arthrodesis is achieved. These "interbody fusion devices" have taken many forms, but many have had difficulty in achieving fusion, at least without the aid of some additional stabilizing device, such as a rod or plate. Moreover, some of these devices are not structurally strong enough to support the heavy loads and bending moments applied at the most frequently fused vertebral levels, namely those in the lower lumbar spine.

The interbody fusion devices (IBFDs) that have overcome these difficulties are typically bulky, at least with respect to the intervertebral space. In particular, these devices have been configured to completely fill the space and to restore the normal spinal anatomy at the instrumented level. One drawback of this approach is that the implant device is not exactly sized to the anatomy of the particular patient, thus typically requiring pre-distraction of opposed vertebrae in order to increase the disc space for device implantation. While a collection of differently sized IBFDs can be provided, it is unwieldy and impractical to provide an IBFD sized for every intervertebral disc space height.

Another drawback of these prior devices is that the surgical insertion site must be at least as big as the IBFD. Minimally invasive and working channel surgical techniques have been recently developed that have significantly reduced the surgical invasion, but even more improvement is needed. One solution to these drawbacks was presented in U.S. Pat. No. 6,595,998 (the '998 Patent), entitled "Tissue Distraction Device", which issued on Jul. 22, 2003, to the assignee of the present invention. The '998 Patent discloses sequentially introducing a series of wafers into the space (whether inter- or intra-vertebral) using a percutaneous introducer. In certain embodiments, the wafers included features that allowed adjacent wafers to interlock to some degree along the longitudinal axis of the wafers. The disclosure of the '998 Patent is incorporated herein by reference, particularly as it pertains to the interlocking features of the wafers and the percutaneous introducer.

In an improvement on the wafer concept in the '998 Patent, an expandable distraction device was disclosed in co-owned pending application U.S. application Ser. No. 10/813,819 (the '819 Application), which was filed on Mar. 31, 2004, and published as U.S. Patent Application Publication No. 2005/0187559 on Aug. 25, 2005. The disclosure of the '819 Application is incorporated herein by reference. The expandable distraction device disclosed in the '819 Application includes a plurality of wafers that are successively inserted to form a stack of wafers in a column. The wafers are configured so that a newly inserted wafer lifts the stack of previously inserted wafers, including the superior endplate, until the space has been distracted to a desired height.

A further improvement is disclosed in co-owned pending application U.S. application Ser. No. 11/211,346 (the '346 Application), which was filed on Aug. 25, 2005, and was published as U.S. Patent Application Publication No. 2006/0058807 on Mar. 16, 2006. The disclosure of the '346 Application is incorporated herein by reference. The '346 Application discloses a wafer insertion apparatus 50 that includes a wafer track 52 configured at one end to releasably engage the inferior endplate of the expandable device 10, as depicted in FIG. 1. The other end of the wafer track is connected to a gun 51 that supports a cartridge of wafers 54 and includes a trigger-operated mechanism 53 for extracting a wafer from the cartridge and advancing it along the wafer track into the wafer cavity between the superior and inferior endplates. The wafer insertion apparatus initially supports the expandable device in situ and includes a release plate operable to separate the wafer track from the expandable device when wafer insertion is complete.

The wafer insertion apparatus disclosed in the '346 Application utilizes a series of posts as shown for example in FIGS. 44-45 thereof formed in the wafer cavity defined by the inferior endplate. The posts are engaged by an insertion plate that forms part of the wafer track so that the track can support the expandable distraction device in situ during wafer insertion. A release plate severs the posts to allow the wafer track to disengage the inferior endplate for removal of the wafer insertion apparatus.

The wafers disclosed in the '346 Application include features that facilitate interlocking between adjacent wafers. Thus, as illustrated for example in FIGS. 28-29 and FIGS. 35-36 of the '346 Application, the wafers include resiliently deflectable features that deflect and lock upon longitudinal insertion of a new wafer underneath a previously inserted wafer.

In preferred uses of the expandable devices described above, it is contemplated that bone promotion filler such as osteoinductive or osteoconductive material may be integrated around, and in some cases into, the stack of wafers forming the distraction device. Ideally, once fusion occurs the entire space is rigid, as if the entire space is bone. In an interbody fusion procedure, the vertebrae adjacent the affected disc space are fused together so that the motion segment is eliminated at the disc level. The distracted space is subjected to significant loads, even when efforts are made to immobilize the spine around the affected vertebral level. While the compressive loads along the length of the spine are readily borne by the expanded distraction device and associated wafer stack, transverse loads and most particularly torsion loads must also be withstood.

Consequently, there remains a need for an expandable distraction device that can endure the significant spinal loads and maintain suitable structural integrity, at least until complete fusion can be achieved.

SUMMARY OF THE INVENTION

In order to address these objectives, the present invention contemplates a device for distracting a body tissue space between opposing tissue surfaces, comprising an upper plate having an outer surface configured to contact one of the opposing surfaces and a lower plate having an outer surface configured to contact the other of the opposing surfaces. The upper and lower plates combine to define a cavity when the upper plate is supported on the lower plate. The lower plate includes a support surface for supporting at least one expansion member, or wafer, within the cavity, and a channel communicating with the cavity that is configured to receive an expansion member conveyed therethrough for placement on the surface of the lower plate.

In one embodiment, the wafers are like-configured, each comprising an interlocking engagement that includes a plurality of resiliently deflectable prongs that project above an upper surface of the wafer, and a like plurality of locking surfaces extending transversely between the upper surface and the lower surface. The prongs deflect as each wafer is inserted into the space between the expandable upper and lower plates until each wafer is substantially co-extensive with the prior inserted wafer. When so oriented, the prongs resiliently deflect upward against corresponding locking surfaces to prevent retrograde movement (i.e., opposite the direction of insertion) of the newly inserted wafer.

Each wafer is configured with angled leading and trailing ends so that each newly inserted wafer lifts the stack of prior inserted wafers. As each wafer is inserted, additional interlocking features are engaged that prevent movement of the wafers in other degrees of freedom. One interlocking feature includes a keyway and tab arrangement that prevents further movement along the direction of insertion. Yet another interlocking feature prevents relative movement transverse to the insertion direction and vertically within the stack of wafers. The interlocking features also prevent disengagement of the wafers or dislodgement of any wafer from the stack due to torsional or twisting movement.

In one embodiment, an expansion member for sequential insertion into a space between opposing tissue surfaces to be distracted is provided that comprises an elongated body having an upper surface and an opposite lower surface, at least one locking surface extending transversely between the upper surface and the lower surface, and at least one resilient prong defined in and projecting outwardly beyond one of the upper surface and the lower surface. In one feature, the at least one prong is oriented such that when two of the expansion members are immediately adjacent and substantially co-extensive at least a portion of the at least one prong of one expansion member is disposed in contact against the locking surface of the other expansion member.

In another embodiment, an expandable interbody fusion device (IBFD) for implantation into the intradiscal space between two opposing vertebral bodies of a spine, comprises a first endplate member having an outer surface for contacting one vertebral body in a spine, and a second endplate member having an outer surface for contacting an opposing vertebral body in the spine, the second endplate member being movable in an expansion direction relative to the first endplate member toward the opposing vertebral body. The IBFD further comprises an expansion member configured to be introduced between the first endplate member and the second endplate member in an insertion direction that is substantially perpendicular to the expansion direction, to thereby move the first and second endplate members relatively apart in the expansion direction upon introduction, and an interlocking prong and cavity engagement defined between the expansion member and the second endplate member to prevent relative movement of the expansion member relative to the second endplate member in a direction opposite the insertion direction when the expansion member is substantially co-extensive with the second endplate member. In one aspect of this embodiment, the expansion member includes a surface facing the second endplate member and the second endplate member has a surface facing the expansion member, and the cavity is defined in the facing surface of the second endplate member and the prong projects beyond the facing surface of the expansion member into the recess when the expansion member is substantially co-extensive with the second endplate member.

It is one object of the invention to provide an improved expandable device that may be used to distract the space between two body tissue surfaces. A further object of the invention is to provide expansion members that interlock in multiple degrees of freedom.

One benefit of this feature is that the wafers become interlocked upon sequential insertion. Other objects and benefits of the invention will become apparent upon consideration of the following written description taken together with the accompanying figures.

DESCRIPTION OF THE PREFERRED EMBODIMENTS

Figure 1:
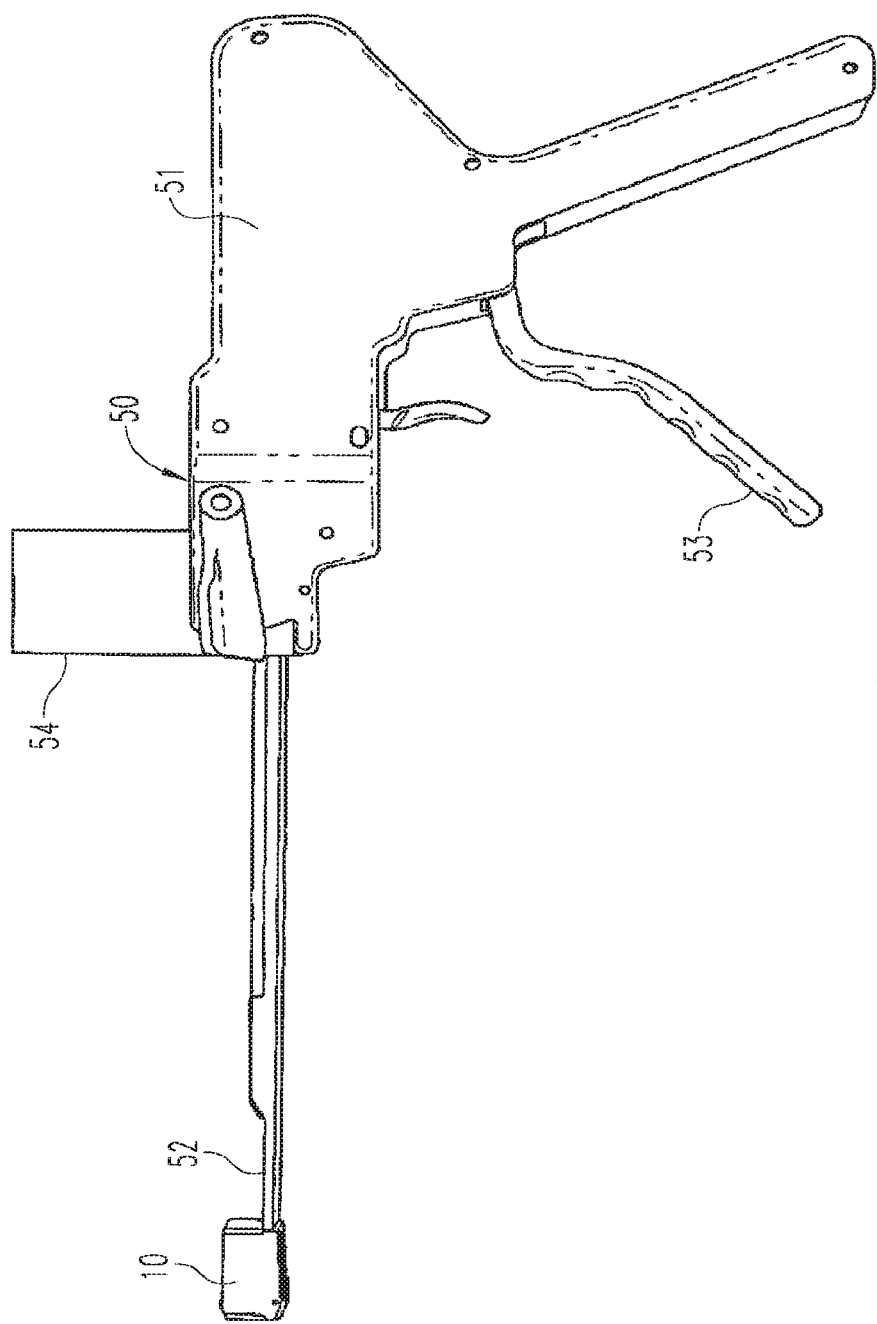
FIG. 1 is a side view of an expandable distraction device mounted on a wafer insertion apparatus as disclosed in co-pending U.S. Patent Application Publication No. 2006/0058807.
Figure 2:
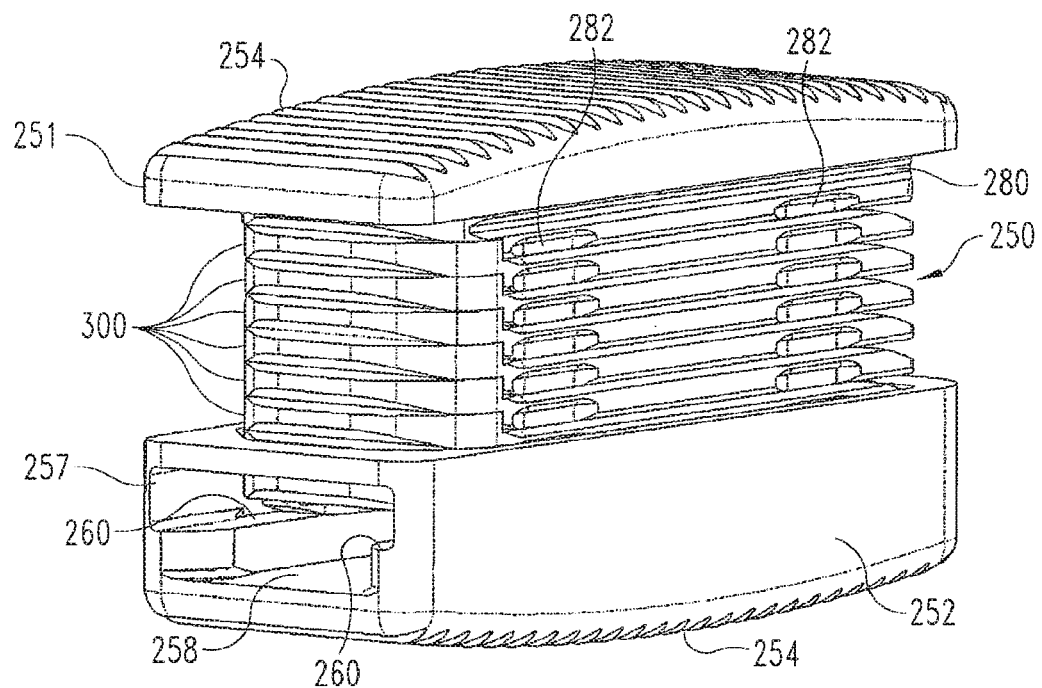
FIGS. 2 and 3 are rear and front perspective views of an expandable distraction device comprising a stack of wafers in accordance with one embodiment of the present invention.
Figure 3:
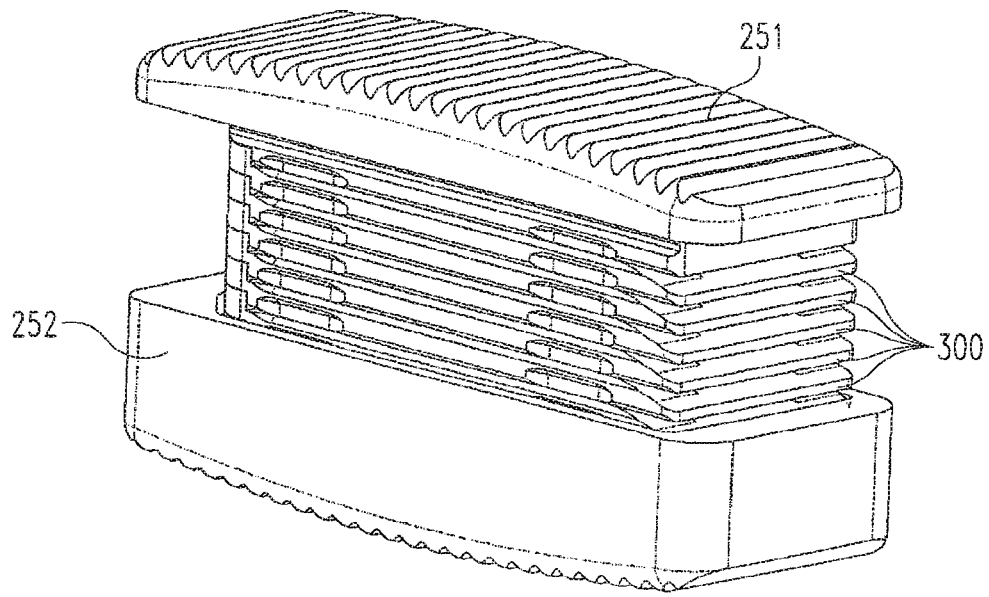
Figure 4:
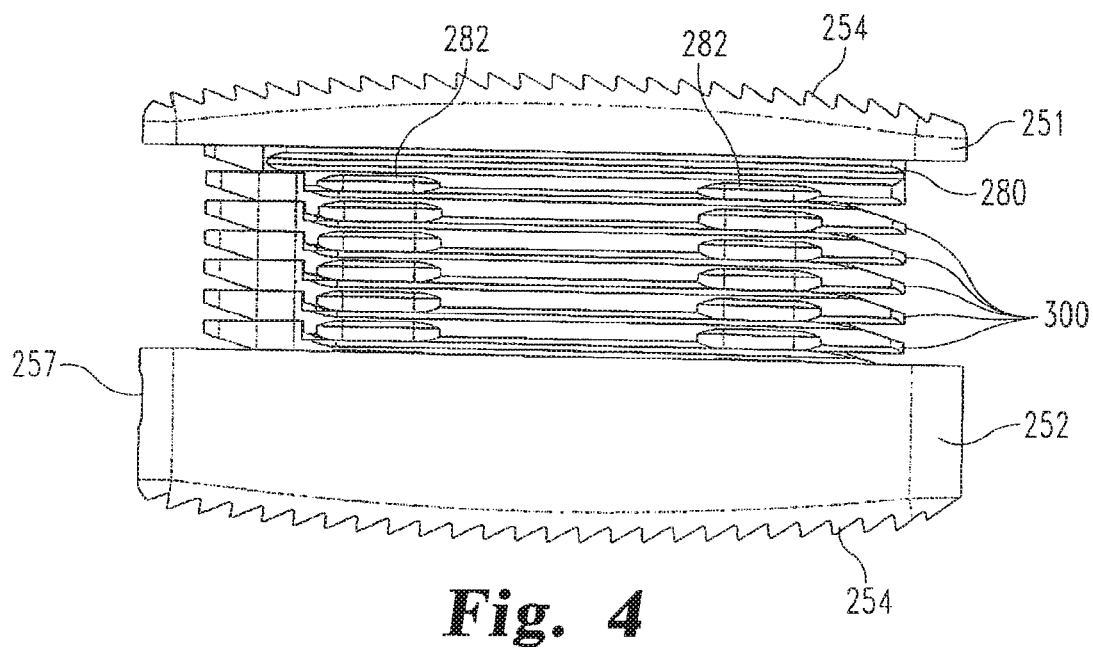
FIGS. 4 and 5 are side and end views of the expanded device shown in FIGS. 2-3.
Figure 5:
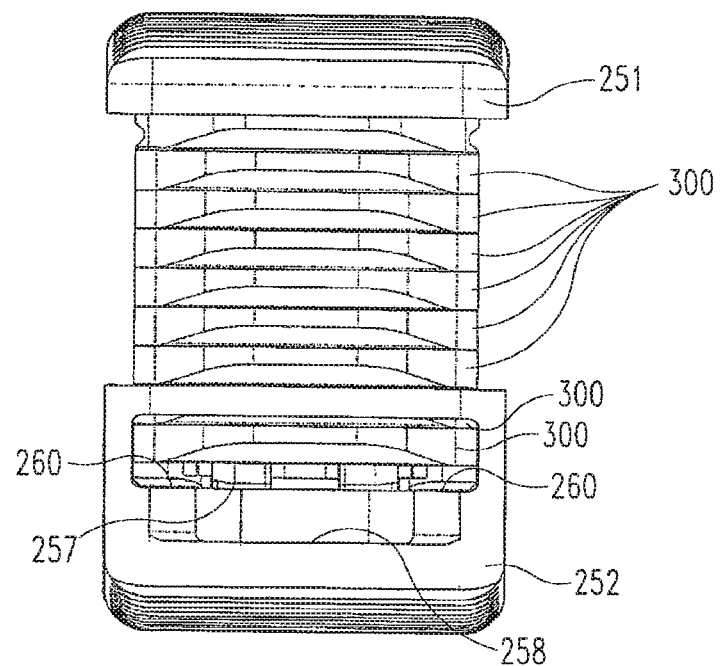

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates an improved interlocking wafer, and particularly a wafer configuration that firmly and permanently interlocks a stack wafers inside an expandable distraction device, even when subjected to normal spinal loads. In accordance with one embodiment of the invention, an expandable distraction device 250 is provided, as shown in FIGS. 2-5, which includes a stack of interlocking wafers 300 that can withstand spinal loads. The distraction device 250 includes a superior endplate 251 and an inferior endplate 252 that may be similar to the endplates disclosed in the '346 Application, which disclosure is incorporated herein by reference. The surfaces of the endplates include ridges 254 that are adapted to firmly grip the vertebral bodies when the device is expanded to distract the intervertebral space. In the illustrated embodiment, the contours of the endplates are adapted to engage the bony endplates of the adjacent vertebrae.

The inferior plate 252 defines a wafer channel 257 through which the wafers 300 which serve as expansion members are introduced. As with the endplates disclosed in the '346 Application, the inferior endplate defines opposite ledges 260 which support each wafer as it is introduced into the wafer channel, as illustrated in FIG. 7. The inferior endplate also defines an inserter channel 258 that is underneath and in communication with the wafer channel 257. The inserter channel 258 receives a wafer track, such as track 52 shown in FIG. 1. More specifically the inserter channel 258 includes a number of posts 262 projecting upward therein that are configured, as illustrated in FIGS. 6-7, to engage an insertion plate 270 and a release plate 272 in a manner similar to that described in the '346 Application incorporated herein.

Figure 6:
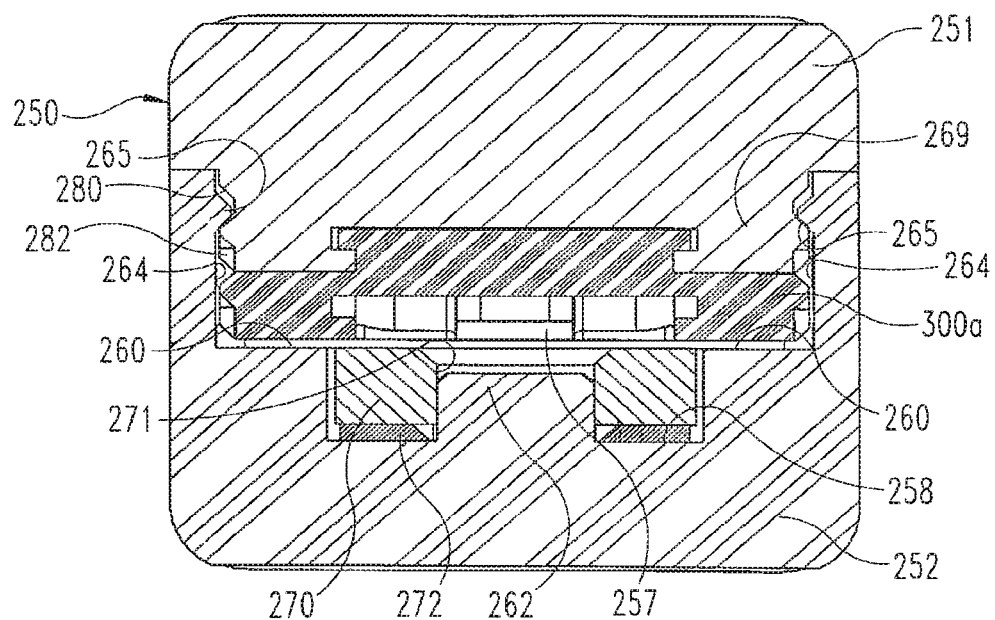
FIG. 6 is an end cross-sectional view of an expandable distraction device such as the device shown in FIGS. 2-5 shown with a single wafer therein prior to expansion of the device.
Figure 7:
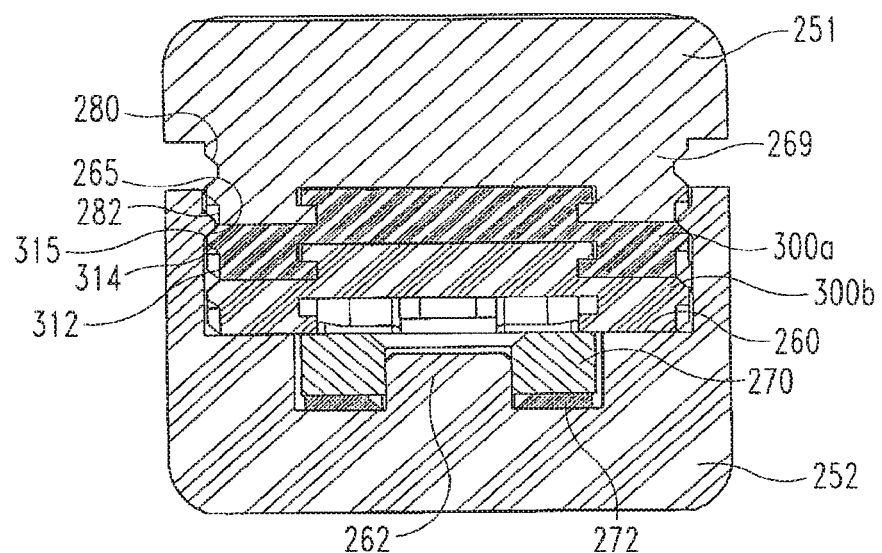
FIG. 7 is an end cross-sectional view of the expandable distraction device depicted in FIGS. 2-5 showing expansion by the introduction of a second wafer into the device.
Figure 16:
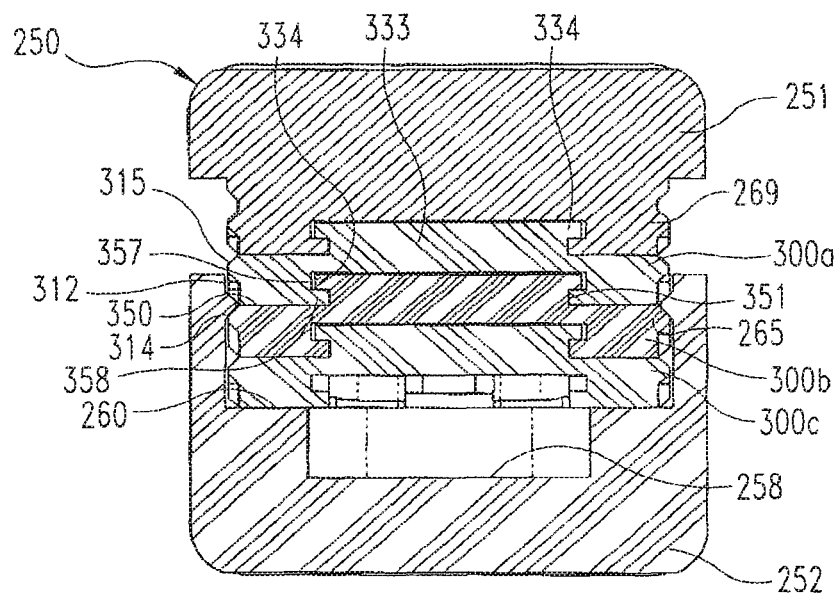
FIG. 16 is an end cross-sectional view of the expandable distraction device depicted in FIGS. 6-7 shown with a three-wafer stack within the device after removal of the wafer track.

The superior and inferior endplates 251 and 252 are configured to be initially releasably engaged when the device 250 is unexpanded, as shown in FIG. 6. In one embodiment, each opposite side wall 264 of the inferior endplate 252 defines a pair of ribs 265 projecting into the wafer channel, the ribs 265 being spaced lengthwise on each side wall 264. The superior endplate 251 includes a hub portion 269 that is sized to fit within the wafer channel 257 and between the side walls 264 of the inferior endplate. The hub portion 269 defines a groove 280 extending along each side of the hub portion that is configured to engage the ribs 265 of the inferior endplate. This engagement temporarily holds the superior and inferior endplates together as the device 250 is introduced into the space to be distracted. The hub portion 269 further defines in a particular arrangement a pair of spaced notches 282 beneath the groove 280 that are also configured to receive the corresponding pair of ribs 265. As shown in FIG. 7, with the ribs 265 extending into the notches 282, the superior endplate 251 is freely separated from the side walls 264 of the inferior endplate 252 and the lower surfaces of the ribs 265 contact the angled upper edges 315 (see FIG. 11) of the side wall 314 of wafer 300a. As such, the ribs 265 provide some resistance against wafer 300a until further wafers are introduced as seen in FIG. 16.

Details of one embodiment of the interlocking wafer 300 are shown in FIGS. 8-14. The wafer 300 has an upper surface 302 and a lower surface 303, both of which are generally planar so that the wafers can form a stable stack within the IBFD 250. The trailing end 305 includes a downward-facing sloped surface 306 that corresponds angularly to an upward-facing surface 309 on the leading end 308 of the wafer. The two sloped surfaces help displace an earlier inserted wafer 300 upon introduction of a new wafer. More specifically, when a wafer is within the wafer channel 257, resting on the ledge 260 (FIG. 7), the downward-facing sloped surface 306 is lifted by contact with the upward-facing slope 309 of a newly inserted wafer. This allows the newly inserted wafer to ride along the ledge 260 until it is positioned fully underneath the previous wafer.

The wafer 300 further includes notches or indentations 312 that are configured to receive the ribs 265 on the side walls of the inferior plate 251 (see FIG. 16) in a manner similar to the notches 282 in the hub portion of the superior endplate 251. In the preferred embodiment, the indentations 312 are offset toward and intersect the lower surface 303. As best seen in FIG. 16, the ribs 265 sit within the indentations 312 of an "upstream" wafer 300a and bear against an upper angled edge 315 of the side walls 314 of the "downstream" wafer 300b underneath. In the illustrated embodiment, two spaced ribs 265 are provided on each side wall of the inferior endplate. Thus, the hub portion of the superior endplate 251 and the wafers 300 include two corresponding notches 312 oriented to receive the ribs. Of course, different numbers of ribs and notches may be provided.

Figure 11:
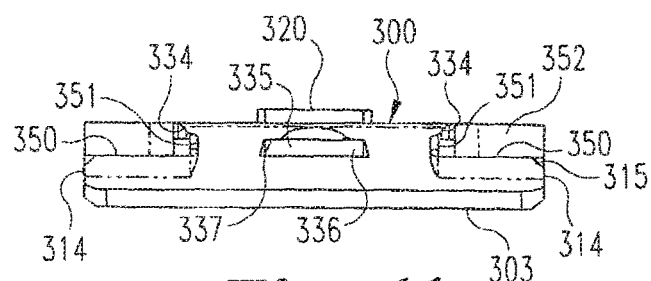
FIG. 11 is an insertion end view of the interlocking wafer shown in FIGS. 8-10.
Figure 12:
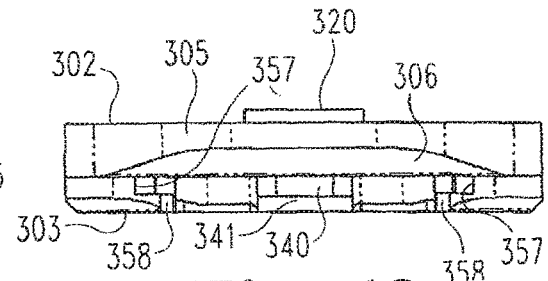
FIG. 12 is a trailing end view of the interlocking wafer shown in FIGS. 8-10.
Figure 15:
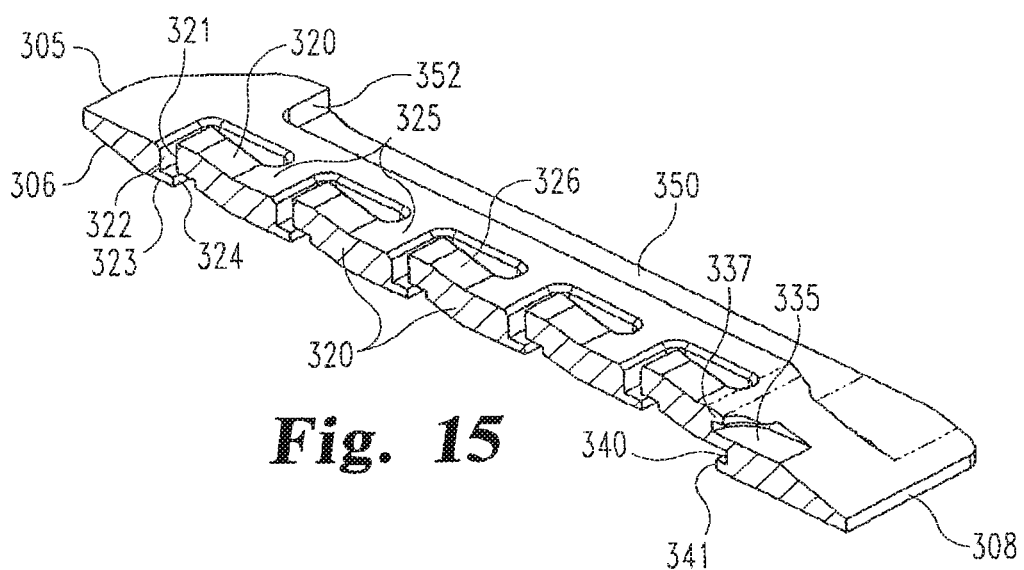
FIG. 15 is a longitudinal perspective cross-sectional view of the interlocking wafer depicted in FIGS. 8-14.
Figure 17:
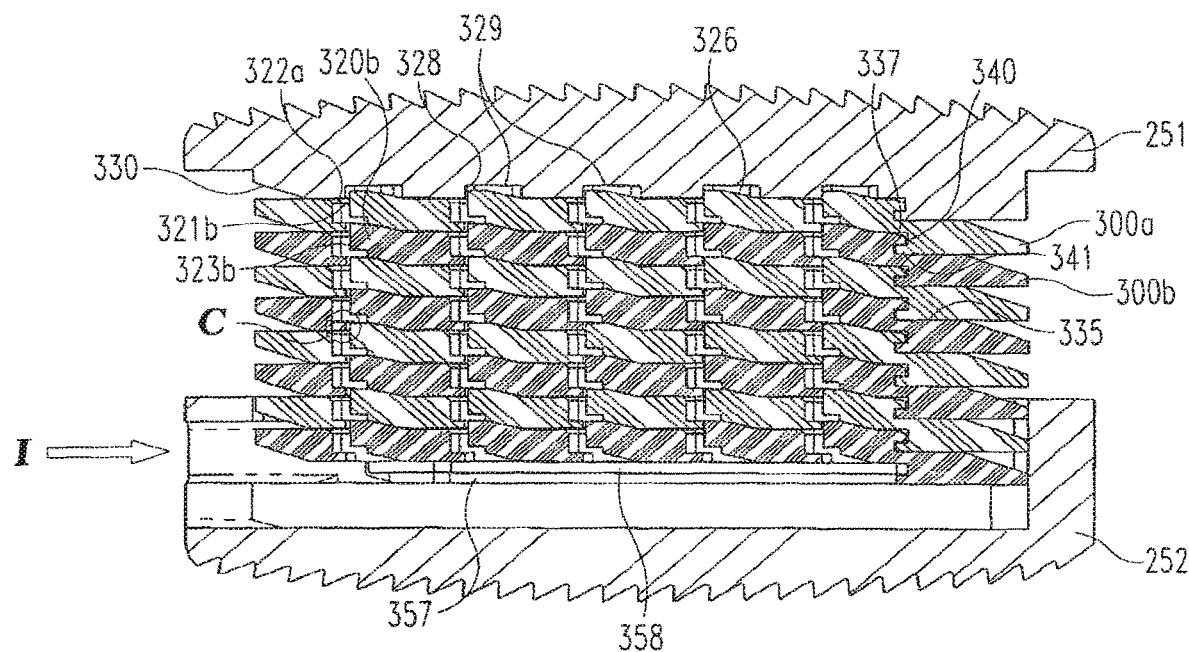
FIG. 17 is a side cross-sectional view of an expandable distraction device, such as the device shown in FIGS. 2-5, with a stack of interlocking wafers of the present invention disposed within the device.

The wafer 300 includes several features to interlock adjacent wafers in multiple degrees of freedom. One particular feature includes a series of resiliently deflectable prongs 320 that project outwardly above the upper surface 302 of the wafer (as best seen in FIGS. 11-12). In one arrangement, the prongs 320 are disposed generally centrally on the central portion 333 of each wafer 300, extending lengthwise in alignment. Each prong 320 is seated within a cavity 322 defined through the wafer. Each prong is cantilevered from an adjoining wall 325 between cavities, as best seen in FIGS. 15 and 17, so that the prong can deflect into the cavity upon pressure on the prong from above the wafer. The cavity 322 includes a rear ledge 323 at the lower surface 303. In certain embodiments, the rear ledge may extend sufficiently far into the cavity beneath the prong 320 to keep the prong from bending underneath the wafer. More importantly, the rear ledge 323 defines a stop surface 324 at the lower surface 303 of the wafer against which the cantilevered face 321 of an associated prong bears. In the illustrated embodiment, five prongs 320 and associated stop surfaces 324 are provided on each wafer to provide a firm interlocking engagement between adjacent wafers. Of course, it is contemplated that fewer or greater numbers of prongs may be provided in a wafer within the scope of the present invention. For instance, the number of prongs may be adjusted based on the length of the wafer 300.

Thus, as shown in FIG. 17 an uppermost wafer 300a provides a stop surface 324a that is contacted by the cantilevered face 321b of the next lower wafer 300b as the prong 320b of that lower wafer projects into the cavity 322a of the upper wafer. It can be appreciated that each of the five prongs 320b of the wafer 300b shown in FIG. 17 project into a corresponding cavity 322a and engage the associated stop surface 324a to lock the wafers against retrograde movement—i.e., movement opposite the direction of insertion I—that might lead to expulsion of the wafer from within the expanded device 250. It should be appreciated that as each subsequent wafer is sequentially inserted, the associated prongs 320b deflect downward against the associated ledge 323b as the prongs progressively traverse the lower surface 303a of a previously inserted wafer 300a. Preferably, the prongs are provided with an angled surface 326 that bears against the underside of the previous wafer and progressively deflects the prong as the angled surface traverses the other wafer. Once the prongs in the lower wafer 300b are aligned with the cavities 322a in the upper wafer, the prongs spring upward into the cavity 322 of the previous wafer to positively and substantially permanently lock the two wafers together in the direction of insertion I.

As shown in FIG. 17, each wafer in the stack locks into the immediately previously inserted wafer using the prongs and stop surface. The uppermost wafer 320a also engages the superior endplate 251 to lock the stack to the expandable device 250. Thus, in one embodiment, a stop surface 328 is formed in corresponding recess 329 defined in the underside of a hub portion 269 of the superior plate 251. The hub 269 is also provided with a downward-facing sloped surface 330 similar to the sloped surface 306 of the wafers, to facilitate introduction of the initial wafer 300a and to lift the superior endplate as that initial wafer is introduced. Thus, it can be seen that the superior plate 251 and the successively inserted stack of wafers 300 are all interlocked against longitudinal movement opposite the direction of insertion I.

Figure 13:
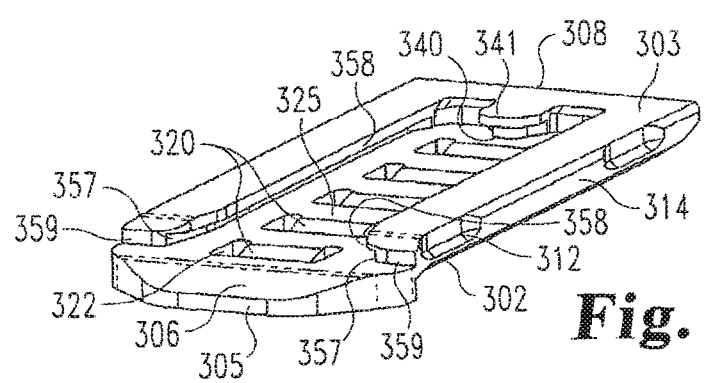
FIGS. 13-14 are perspective and plan views of the bottom of the interlocking wafer shown in FIGS. 8-10.
Figure 14:
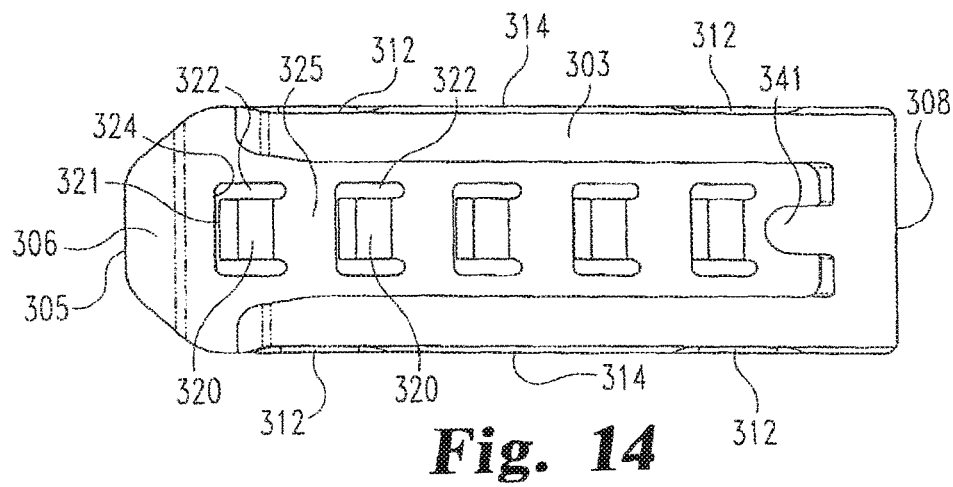

The cooperating locking structure of the wafers 300 also restricts or prevents movement of the wafers in the stack in the direction of insertion I. In one embodiment, the upper surface 302 defines a keyway 335 with side channels 336 and an upper wall 337, as shown in FIGS. 11, 15 and 17. The lower surface 303 defines a complementary notch 340 and tab 341, as shown in FIGS. 13-14. The tab 341 fits within the side channels 336 and the notch engages the upper wall 337 of the keyway, as seen in FIG. 17. Thus, the tab and keyway prevent longitudinal movement of each wafer relative to the previously inserted wafer in the direction of insertion I. As shown in FIG. 17, there may be some clearance C between the cantilevered face 321 of the prongs 320 and the corresponding stop surfaces 324 of the wafers. The overlapping engagement between the keyway 335 and the notch 340 and tab 341 is sufficient so that any retrograde movement of the wafers that closes this clearance will not disengage the tab from the keyway. It is contemplated that the clearance C between prongs and stop surfaces may decrease from the trailing end 305 to the leading end 308 of the wafer, as depicted in FIG. 17, to enhance the rigidity of the engagement between wafers.

Figure 8:
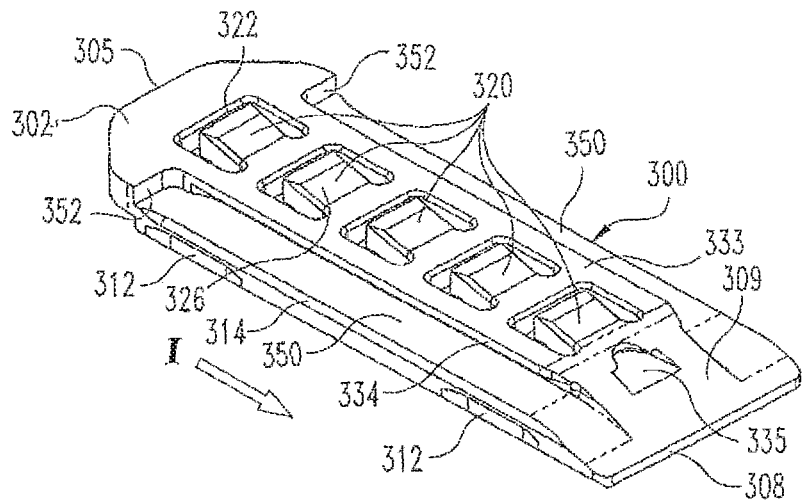
FIG. 8 is a perspective view of an interlocking wafer in accordance with one embodiment of the present invention that is configured to form a wafer stack within an expandable distraction device, such as the device shown in FIGS. 2-5.
Figure 9:
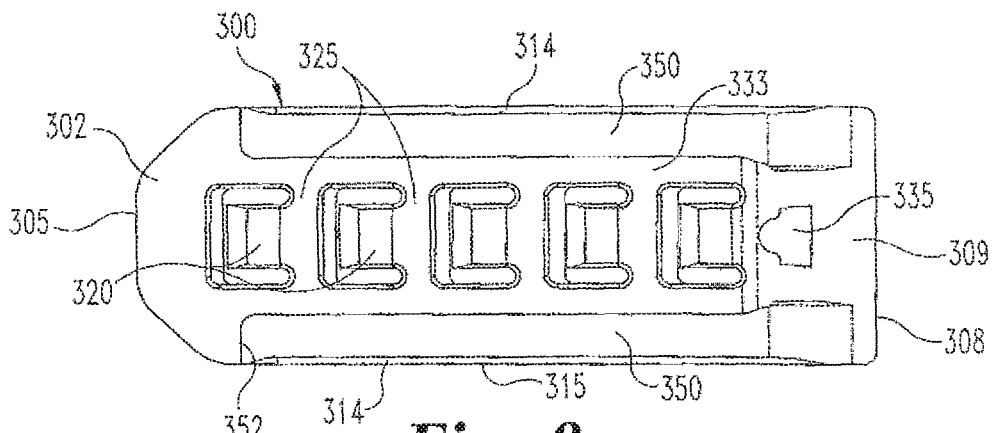
FIG. 9 is a top view of the interlocking wafer shown in FIG. 8.
Figure 10:
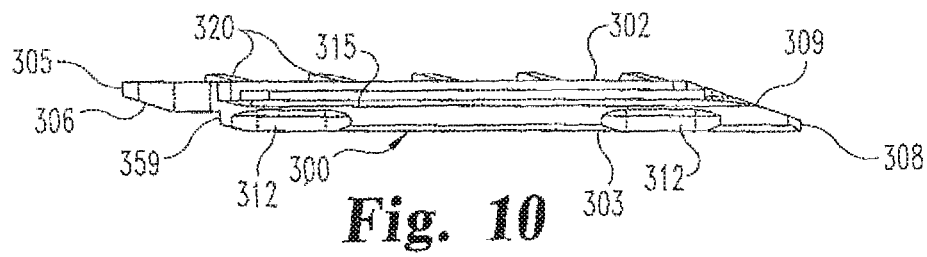
FIG. 10 is a side view of the interlocking wafer shown in FIGS. 8-9.

As thus far described the wafer stack is locked against movement in the longitudinal direction (i.e., fore and aft relative to the insertion direction I). Certain embodiments of the locking structure described herein further contemplate restricting or preventing relative movement between wafers in multiple degrees of freedom. Thus, in one embodiment, the upper surface 302 includes a channel 350 formed at each lateral side of the wafer 300 flanking the central portion 333 that carries the prongs 320, as seen in FIGS. 8-9. The central portion 333 extends into a flange 334 overhanging each channel that forms a groove 351 contiguous with the channel 350 (FIG. 11) thereby defining a T-bar configuration). The channel and groove on each side of the wafer extends from the leading end 308 to a stop face 352 adjacent the trailing end 305.

The bottom surface 303 of each wafer defines features for mating with the T-bar configuration on the upper surface 302 of a successive wafer. Thus, as shown best in FIGS. 13 and 16, the bottom surface includes a center track 357 with side flanges 358 that correspond define a T-slot configuration which corresponds to and slidably mates with the T-bar configuration on the upper surface of an immediately adjacent wafer 300, with flanges 334 being received in the track 357. It should be appreciated that the respective T-bar and T-slot configurations may be formed on either the upper surface or the lower surface of a wafer as desired. This interlocking relationship restricts or prevents transverse or lateral movement of one wafer relative to adjacent wafers. It can also be appreciated that the interaction between the track 357 and side flanges 334 also restricts or prevents vertical separation between wafers. This interlocking engagement occurs automatically when one wafer is introduced into the IBFD 250 underneath and substantially co-extensive lengthwise with a previously inserted wafer. The stop face 352 stops the linear advancement of one wafer relative to the other when the end surface 359 (FIG. 13) abuts the stop face. The length of the channel is calibrated so that the end faces 359 of the underneath wafer reach the stop faces 352 after the prongs 320 have engaged the corresponding cavities 322 in the immediately preceding wafer.

Figure 18:
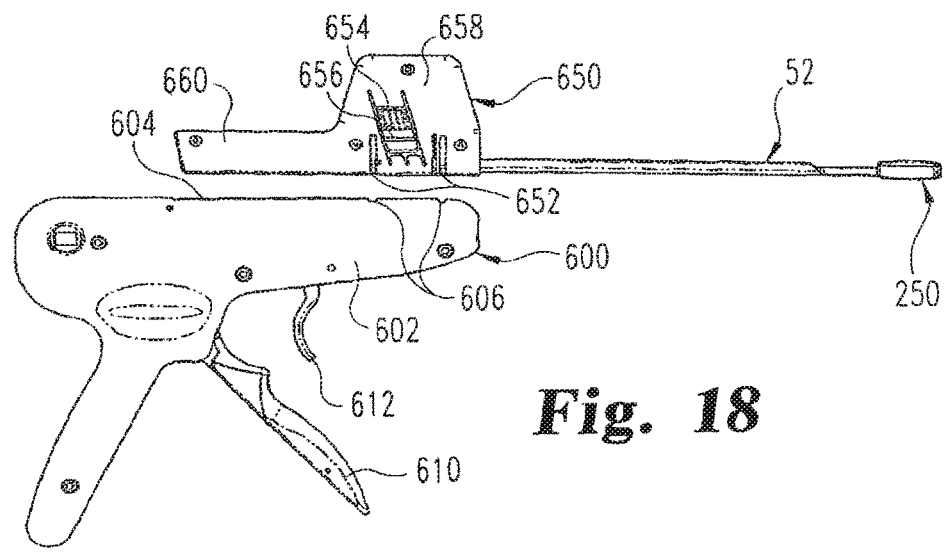
FIG. 18 is an exploded side view of a wafer inserter apparatus and a wafer cartridge suitable for introducing interlocking wafers of the present invention into an expandable distraction device.

As shown in FIG. 7, the lowermost wafer 300b rests on the wafer support ledges 260 defined in the inferior plate 252. As more particularly disclosed in the '346 Application, the wafers are directed onto these support ledges by passage along a wafer track assembly, such as the track assembly 52 shown in FIG. 18. In the view shown in FIG. 7, the posts 262 are intact and an insertion plate 270 is shown within the insertion channel 258 with the posts 262 projecting through corresponding holes 271 in the plate. The insertion plate extends through the wafer track 52 for engagement with the mechanism of the inserter gun 600 (FIG. 18). In one embodiment, the openings 271 are configured with a cutting edge so that upon withdrawal of the insertion plate, the posts 262 are severed. Alternatively, a release plate 272 may be provided underneath the insertion plate, as shown in FIGS. 6-7. In this instance, the release plate is retracted beneath the insertion plate to sever the posts. Once the posts have been severed, the track assembly 52 may be disconnected from the completed distraction device 250. The resulting IBFD 250 with the stacked wafers 300 appears as shown in FIGS. 2-5, and in FIGS. 16-17.

The manner in which the IBFD 250 is formed is illustrated in the sequence shown in FIGS. 6, 7, 16 and 17. In FIG. 6 the superior endplate 251 is shown with one wafer 300a already engaged to the hub 269. In this condition, IBFD 250 is unexpanded and is attached to the track assembly 52 as depicted in FIG. 18. In one embodiment, the expandable device is initially provided with this wafer in place and the superior and inferior endplates releasably connected by way of the groove 280 and ribs 265. When the first inserted wafer 300b is introduced into the device, the newly inserted wafer lifts the first wafer 300a and the superior endplate 251 until the angled edges 315 of the side walls 314 of the first inserted wafer 300b contact the ribs 265, as shown in FIG. 7. When a second wafer 300c is inserted, as shown in FIG. 16, the first wafer 300a is pushed above the inferior endplate, while which the angled edges 315 of the second wafer 300b now engage the ribs. This process continues with each successively inserted wafer until a complete stack if formed, as depicted in FIG. 17. It should be appreciated that the trailing end of a previously inserted wafer may tend to elevate before the insertion end as a successive wafer is inserted, especially where the wafers are relatively rigid. In such situation, the ribs 265 adjacent the front end will continue to apply resistance to the front end of the forming wafer stack even if the back end is initially separated from the ribs 265 at the back end of the stack.

The wafers may be incorporated into a cartridge 650 that is adapted to releasably fit into a wafer insertion device 600 shown in FIG. 18. The device 600 may incorporate the same internal mechanism within housing 602 that is incorporated into the wafer insertion device disclosed in the '819 Application incorporated by reference above. Specifically, the mechanism is operable to withdraw a wafer from the cartridge and propel successive wafers along wafer track assembly 52 into an IBFD 300 that is preloaded onto the end of the track assembly. It is understood that the device 600 is preferably a reusable instrument, while the cartridge 650 may be reusable or disposable.

The wafer insertion device 600 includes a gun housing 602 that defines a top opening 604 for receiving the cartridge 650. The cartridge includes a pair of vertical ribs 652 on both sides of the cartridge that slidably mate with corresponding internal grooves 606 formed in the gun housing 602. The cartridge is further provided with a resilient latch 654 with a catch end 656 on each side of the cartridge that engages the housing 602. The latch can be manually depressed to release the cartridge from the gun when the IBFD 300 has been fully loaded with a stack of wafers. The cartridge 650 includes a wafer housing 658 that supports a supply of wafers, and a track housing 660 projecting from the wafer housing. The track housing 660 may incorporate portions of the advancement mechanism and guide tracks disclosed in the '819 Application incorporated by reference. The trigger 610 operates the mechanism to extract and advance a wafer along the track 52. The second trigger 612 is connected to the insertion plate 270 (or alternatively the release plate 272) to retract the plate when the wafer stack is complete in order to sever the posts 262, as described above.

It can be appreciated that the interlocking wafer 300 of the present embodiment provides for interlocking engagement that prevents or significantly restricts relative movement in multiple degrees of freedom, including longitudinally, transversely and vertically relative to the wafer body. In addition, the engagement between the prongs and the stop surfaces is maintained even when the wafers are subject to torsion either along the longitudinal axis of the wafer or along a perpendicular axis. All of the interlocking structural features are calibrated to automatically engage once a newly inserted wafer is fully aligned beneath the previously inserted wafer.

The rigid interlocking engagement as described is provided to prevent dislodgement of any wafer in the stack when the expanded IBFD is subjected to the normal spinal loads. Filler material may be introduced into the space surrounding the expanded device 250, such that the filler material in conjunction with the expanded device 250 will form a rigid structure between the adjacent bone surfaces. Thus, once this rigid structure is created (such as by hardening of a filler material or fusion of natural bone within the space) the spinal loads are borne by the entire rigid structure.

Figure 19:
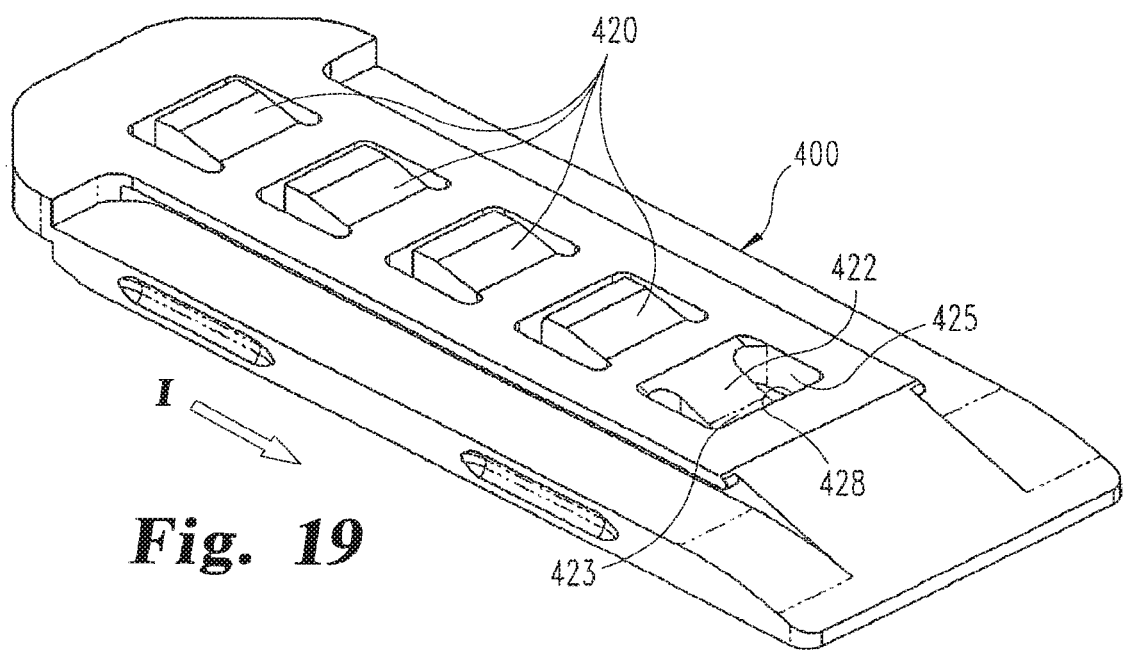
FIGS. 19-20 are a top and bottom perspective views of an alternative interlocking wafer in accordance with a further embodiment of the invention.
Figure 20:
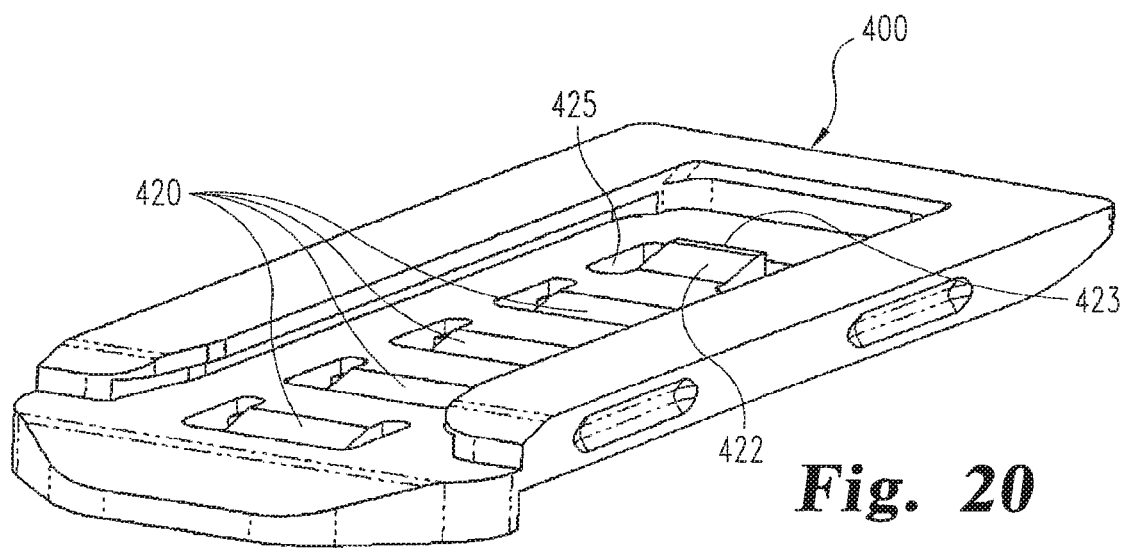

In an alternative embodiment, an interlocking wafer 400 is substantially similar in construction to the wafer 300, except that the wafer 400 shown in FIGS. 19-20 eliminates the keyway 335 of the prior wafer. The wafer 400 includes multiple prongs 420 that are configured and operate the same as the prongs 320 of the prior embodiment. In lieu of the keyway configuration, the wafer 400 reverses the orientation of the forward-most prong 422 so that the forward portion 423 engages a stop face 428 of the recess 425 surrounding the prong. Thus, it can be seen by comparing the prong 422 to the other prongs 420 that the forward-most prong faces in the direction of insertion, rather than opposite, and is configured to deflect upward, rather than downward, as a subsequent wafer is inserted underneath. Once the subsequent wafer is disposed fully underneath the wafer 400, the forward-most prong 422 snaps into the recess 425 of the underneath wafer. The interaction between the forward portion 423 and the stop surface 428 prevents further forward movement of the upper wafer relative to the underneath wafer in the insertion direction I.

Figure 21:
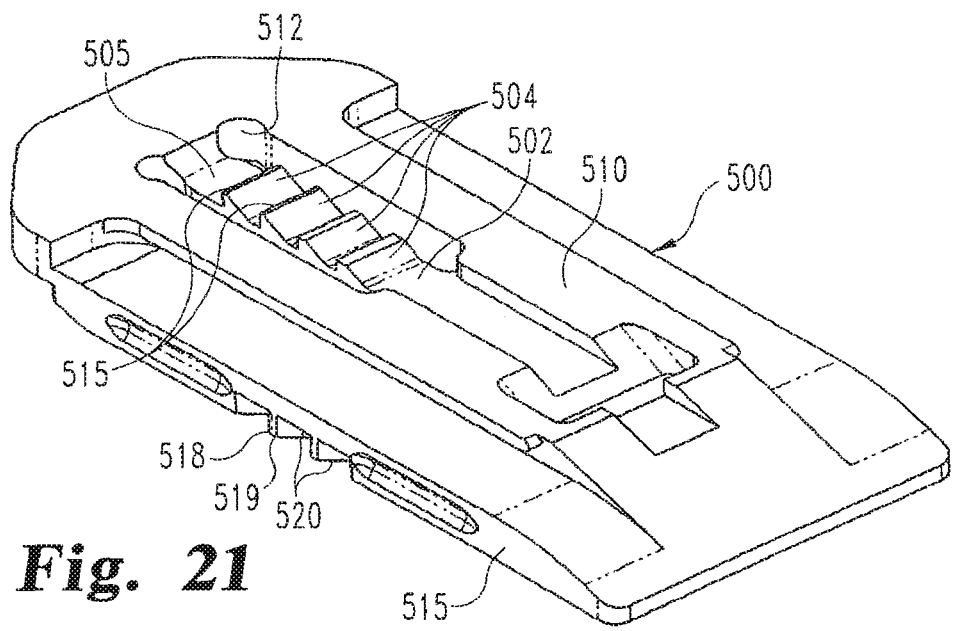
FIGS. 21-22 are top and bottom perspective views of another interlocking wafer in accordance with a further embodiment of the invention.
Figure 22:
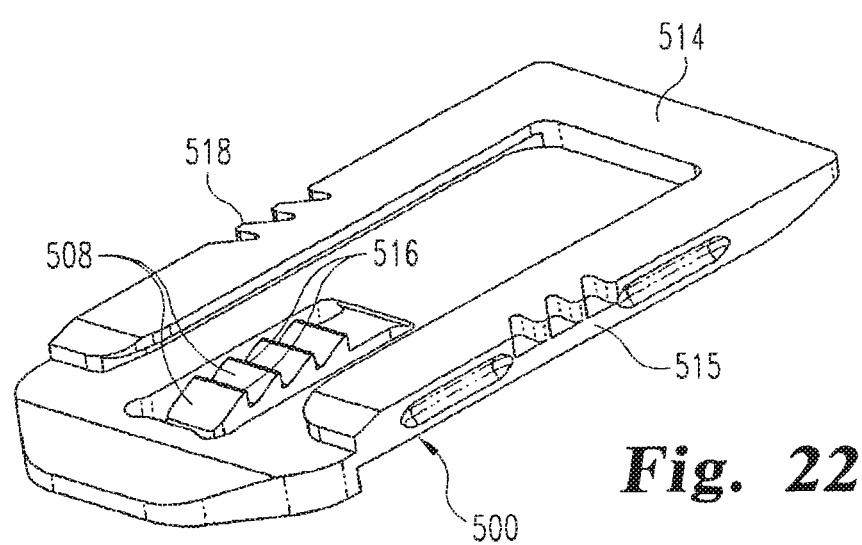

In another embodiment, an interlocking wafer 500 is provided as shown in FIGS. 21-22. This interlocking wafer includes a generally centrally disposed flexible strip 502 that includes a series of sloped ridges 504 on an upper face 505 of the strip and a complementary offset series of sloped ridges 508 on a lower face 506 of the strip. The strip is recessed from the upper surface 510 of the wafer 500 within a cavity 512 formed through wafer. The ridges 508 project below the bottom surface 514 of the wafer so that they can engage the upward-facing ridges 504. The flexible strip 502 resiliently flexes as the upward-facing and downward-facing sloped ridges pass over each other until the end faces 515 of the ridges 504 are abutting the end faces 516 of the lower ridges 508. The abutting end faces 515 and 516 prevent retrograde movement between the two wafers.

The wafer 500 may incorporate other interlocking features found in the wafer 300 that limit transverse and superior-inferior movement of adjacent wafers. In an additional feature, the side walls 515 may incorporate wafer removal features 518. In the illustrated embodiment, these wafer removal features are in the form of ridges 519 with pockets 520 between the ridges that are formed for access by a suitable tool for removal of a wafer if necessary.

It is contemplated that each of the wafers 300, 400, and 500 described herein is formed of a biocompatible material that is sufficiently rigid to form a solid stack within the expandable distraction device, but that has sufficient resilient properties for the prongs to deflect under manual pressure as the successive wafers are inserted into the device. Thus, in one specific embodiment, the wafers are formed of PEEK or a carbon-fiber reinforced PEEK, or similar polymeric material. Preferably, the material is suitable for forming the wafers in a molding process, with little or no machining required to create the various features of the wafers. As an alternative, the prongs 320 and adjoining wall 325 may be formed of a resilient material with the remainder of the wafer 300 being over-molded with a different material that does not require the resilient properties of the prongs. The superior and inferior plates 251, 252 are also formed of a biocompatible material, which may be the same as the wafers. Alternatively, the superior and inferior plates may be formed of a biological material, such as a bone graft material, or an osteoconductive or osteoinductive material The wafers may be formed from a solid form of bone filler material, and/or any other suitable material such as, but not limited to, implantable grade alloys, medical grade composites, medical grade polymers, ceramics, hydrogels and resorbable polymers. The wafers may be dense or porous, while porous wafers may be filled with resorbable polymers, drug therapies or osteoinductive agents.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. For instance, while the illustrated embodiments have been directed to interbody fusion of the spine, the expandable devices and wafers disclosed herein may be used in other applications that require distraction of tissue surfaces. Modifications in size may be necessary depending upon the body space being distracted.

For example, the prongs 320 of the wafer 300 may be oriented to project below the lower surface 303 of the wafer. With this orientation, the passage of a wafer underneath a previously inserted wafer will resiliently deflect the downward projecting prongs until all of the cavities 322 align with all of the prongs. If the orientation of the prongs is altered, it is necessary to also alter the hub 269 of the superior plate 251 of the IBFD 250 to include downward projecting prongs in lieu of the recesses 329. Moreover, as suggested by the wafer 400 shown in FIGS. 19-20, the prongs on the wafer 300 may be oriented to project above and below the wafer.

In the wafer 300, the prongs 320 are situated within cavities 322 that extend through the wafer. Alternatively, prongs may be disposed within a cavity that does not pass through the thickness of the wafer. In this instance, the stop surface 324 may defined in a separate recess formed in the lower surface 303 of the wafer.

What is claimed is:

1. An expandable interbody fusion device for implantation into the intradiscal space between two opposing vertebral bodies of a spine, comprising:
   a first elongate endplate member having an outer surface for contacting one vertebral body in a spine, an opposite lower surface including a downwardly-facing sloped surface thereon, and a bottom surface;
   a second elongate endplate member aligned in the axial direction with said first elongate endplate member and having an outer surface for contacting an opposing vertebral body in said spine, said first elongate endplate member and said second endplate member being movable relatively away from each other in an expansion direction generally transverse to said axial direction; and
   an elongate expansion member having a leading end, a trailing end, and intermediate portion joining said leading end and said trailing end with a longitudinal axis extending along its length, said elongate expansion member being movable between said first elongate endplate member in a first axial direction along said longitudinal axis that is substantially perpendicular to said expansion direction, said expansion member including thereon a sloped surface adjacent said leading end defining a lifting surface operable upon movement of said expansion member in the first axial direction to engage the downwardly-facing sloped surface on said lower surface of said first elongate endplate member to move said first elongate endplate member away from said second elongate endplate member in the expansion direction and expand said device, said expansion member having a plurality of cavities extending through said intermediate portion along said longitudinal axis between said leading end and said trailing end, and wherein said expansion member comprises a portion for coupling with one of said first elongate endplate member or said second elongate endplate member.

2. The expandable interbody fusion device of claim 1, further including a feature to resist retrograde movement of said expansion member during expansion of said device in a second direction opposite first direction.

3. The expandable interbody fusion device of claim 1, wherein said sloped surface is planar and substantially parallel.

4. The expandable interbody fusion device of claim 1, wherein said expansion member comprises a portion for coupling with said first elongate endplate member.

5. The expandable interbody fusion device of claim 4, wherein said portion for coupling comprises a flange on one of said expansion member or said first elongate endplate member slidably extending into a groove formed into the other of said expansion member or said first elongate endplate member.

6. The expandable interbody fusion device of claim 5, wherein said portion for coupling defines a T-bar configuration slidably matable with a T-slot configuration.

7. The expandable interbody fusion device of claim 4, wherein said portion for coupling comprises a flange on one of said expansion member or said second elongate endplate member slidably extending into a groove formed into the other of said expansion member or said second elongate endplate member.

8. The expandable interbody fusion device of claim 7, wherein said portion for coupling defines a T-bar configuration slidably matable with a T-slot configuration.

9. The expandable interbody fusion device of claim 1, wherein said plurality of cavities extending through said intermediate portion do not extend through said sloped surface.

10. The expandable interbody fusion device of claim 1, wherein said intermediate portion includes a generally flat, non-sloped planar surface substantially parallel to said first axial direction.

11. The expandable interbody fusion device of claim 1, wherein said elongate expansion member is a one-piece member.

12. An expandable interbody fusion device for implantation into the intradiscal space between two opposing vertebral bodies of a spine, comprising:

a first elongate endplate member having an outer surface for contacting one vertebral body in a spine, an opposite lower surface including a downwardly-facing engagement surface thereon;

a second elongate endplate member aligned in the axial direction with said first elongate endplate member and having an outer surface for contacting an opposing vertebral body in said spine, said first elongate endplate member and said second endplate member being movable relatively away from each other in an expansion direction generally transverse to said axial direction; and an elongate one piece expansion member having a leading end, a trailing end, and intermediate portion joining said leading end and said trailing end with a longitudinal axis extending along its length, said elongate expansion member being movable between said first elongate endplate member in a first axial direction along said longitudinal axis that is substantially perpendicular to said expansion direction, said expansion member including thereon a sloped surface adjacent said leading end defining a lifting surface configured upon movement of said expansion member in the first axial direction to engage the downwardly-facing engagement surface on said lower surface of said first elongate endplate member to move said first elongate endplate member away from said second elongate endplate member in the expansion direction and expand said device, said expansion member comprising a locking surface for locking engagement with one of said first elongate endplate member or said second elongate endplate member to resist retrograde movement of said expansion member upon expansion of said device in a second direction opposite first direction, said intermediate portion having at least one cavity extending therethrough.

13. The expandable interbody fusion device of claim 12, wherein said locking surface comprises a projection and said first elongate endplate member or said second elongate endplate member has an opening for retentive receipt of said projection.

14. The expandable interbody fusion device of claim 12, wherein said expansion member has a plurality of cavities extending through said intermediate portion along said longitudinal axis between said leading end and said trailing end.

15. The expandable interbody fusion device of claim 12, wherein said expansion member comprises a portion for coupling with one of said first elongate endplate member or said second elongate endplate member.

16. The expandable interbody fusion device of claim 15, wherein said portion for coupling defines a T-bar configuration slidably matable with a T-slot configuration.

* * * * *